US00PP15108P2

(12) United States Plant Patent
Cross

(10) Patent No.: US PP15,108 P2
(45) Date of Patent: Aug. 24, 2004

(54) BEGONIA PLANT NAMED 'BONFIRE'

(50) Latin Name: *Begonia boliviensis*
Varietal Denomination: Bonfire

(75) Inventor: Richard James Cross, Christchurch (NZ)

(73) Assignee: New Zealand Institute for Crop & Food Research Limited (NZ)

( * ) Notice: Subject to any disclaimer, the term of this patent is extended or adjusted under 35 U.S.C. 154(b) by 0 days.

(21) Appl. No.: 10/373,814

(22) Filed: Feb. 27, 2003

(51) Int. Cl.[7] ..... A01H 5/00
(52) U.S. Cl. ..... Plt./343
(58) Field of Search ..... Plt./343

(56) References Cited

PUBLICATIONS

UPOV–ROM GTITM Computer Database 2003/05, GTU Jouve Retrieval Software, Citation for 'Bonfire'.*

* cited by examiner

*Primary Examiner*—Anne Marie Grunberg
*Assistant Examiner*—Annette H Para
(74) *Attorney, Agent, or Firm*—Fulwider Patton Lee & Utecht, LLP

(57) ABSTRACT

A new and distinct cultivar of Begonia named 'Bonfire' comprised of hairs on both the upper and lower leaf surface; bright orange-red flower color, RHS 40A; and red margin on serrated leaf edge.

5 Drawing Sheets

Latin name of the genus and species of the plant claimed: *Begonia boliviensis.*
Variety denomination: Bonfire.

BACKGROUND OF THE INVENTION

The present invention relates to a new and distinct cultivar of Begonia plant botanically known as *Begonia boliviensis,* and referred to by the variety denomination 'Bonfire'.

Seeds were obtained from selected wild growing plants in northern Argentina. The area where the seed was collected had many *Begonia boliviensis* plants. The seeds were selected from wild plants primarily on the basis of ornamental appeal. The seeds were taken to New Zealand where they were germinated. The parental cultivar are unknown, unpatented *Begonia boliviensis* seedlings. The new cultivar was isolated by the inventor, Richard James Cross, at Palmerston North and Invermay, New Zealand, by seedling selection primarily on the basis of ornamental appeal.

Following selection of the seedling, the cultivar was propagated vegetatively by grafting. Following several generations of propagated cuttings, uniformity and stability of the selected characteristics was observed. Asexual reproduction initially took place at Palmerston North, New Zealand. Horticultural examination of the present cultivar has demonstrated that the combination of characteristics herein disclosed for Begonia 'Bonfire' are firmly fixed and are retained through successive generations of asexual reproduction.

BRIEF SUMMARY OF THE INVENTION

The following traits have been repeatedly observed and are determined to be basic characteristics of Begonia 'Bonfire', which in combination distinguish this Begonia as a new and distinct cultivar:

1. Hairs on both the upper and lower leaf surfaces;
2. Bright orange-red flower color, RHS 40A; and
3. Red margin on serrated leaf edge.

Begonia 'Firecracker' (unpatented) is the closest comparison variety known to the applicant, however the new cultivar is quite different. Begonia 'Bonfire' differs from 'Firecracker' by having significant hairs on both the upper and lower leaf surfaces, which the gives the foliage a dull appearance in comparison with the bright, hairless, glossy foliage of 'Firecracker'.

BRIEF DESCRIPTION OF THE DRAWINGS

The accompanying color photographic drawings show the unique characteristics of the new cultivar Begonia 'Bonfire', at two years old, with colors as accurate as is possible with color photographs.

The first photographic drawing shows a close-up view of an individual inflorescence of 'Bonfire', depicting the bright orange-red flower color.

The second photographic drawing shows a close-up view of several inflorescences of 'Bonfire'.

The third photographic drawing shows a close-up view of the leaves of 'Bonfire', depicting the serrated, red edge.

The fourth drawing shows a whole plant view of 'Bonfire'.

The fifth drawing shows a whole plant view of several 'Bonfire' plants.

DETAILED BOTANICAL DESCRIPTION

The following observations, measurements, and values describe the new cultivar as grown in Silvan, Victoria, Australia under conditions which approximate those generally used in commercial practice.

Color references are made to The Royal Horticultural Society Colour Chart (RHS) except where the general colors of ordinary significance are used. Colors are approximate as color depends on horticultural practices such as light level and fertilization rate among other things. The plant was two years old when observed for the detailed botanical description.

Origin: Seedling from breeding program.

Parentage:

*Maternal parent.*—Unknown seedling.

*Paternal parent.*—Unknown seedling.

Propagation: Plants have been selected from the original seedling and propagated vegetatively by cutting. Initial selection was made in New Zealand.

Plant:

*Plant habit.*—Semi erect.

*Plant size.*—Medium, height 750 mm; width 1000 mm.

*Growth rate.*—Medium.

*Density.*—Dense.

*Growth type.*—Herbacious perennial.

*Rooting System.*—Characterized by a large irregular-shaped tuber with several robust, succulent, erect stems airing therefrom and relatively small white roots emanating from the lower sides of the tuber. Color is Yellow-orange Group RHS 22D.

Leaf:

*Color.*—Green, RHS 137 A

*Characteristics.*—Hair on both upper and lower leaf surfaces.

*Shape.*—Lanceolate.

*Length.*—110 mm.

*Width.*—40 mm.

*Apex.*—Accuminate.

*Margin.*—Serrate.

*Base.*—Oblique.

*Petiole.*—13 mm in length; red-purple in color, RHS 60B.

Stem:

*Branching arrangement.*—Basal.

*Surface texture.*—Smooth.

*Lenticels.*—None.

Flower:

*Type.*—Single.

*Diameter.*—Small, mean flower diameter is 56 mm.

*Color.*—Bright oranged-red, RHS 40A.

*Time of flowering season.*—Long, spring to autumn.

*Flower profile upper.*—Stellate.

*Flower profile lower.*—Flat.

*Midzone color.*—Orange-red, RHS 30A (outside); orange-red, RHS 33B (inside).

*Margin inside.*—Orange-red, RHS 33A.

*Basal spot.*—Orange-red, RHS 33A.

*Buds.*—Shape: Lanceolate. Length: 17 mm. Width: 15 mm. Color: Yellow, RHS 145B.

*Petals.*—Margin: Unruffled. Number of petals: 4. Size: 2 petals are 50 mm long and 15 mm wide; 2 petals are 66 mm long and 6 mm wide.

*Pedicels.*—Width: 2 mm. Length: 21 mm.

*Calyx.*—Sepals: Not present.

*Stamen.*—Filament: 3 mm in length; yellow in color. RHS 10C.

Reproductive system:

*Seeds.*—Extremely small and "dust-like", typical of *Begonia boliviensis.*

Disease resistance: Moderate.

I claim:

1. A new and distinct Begonia plant named 'Bonfire', as illustrated and described herein.

* * * * *

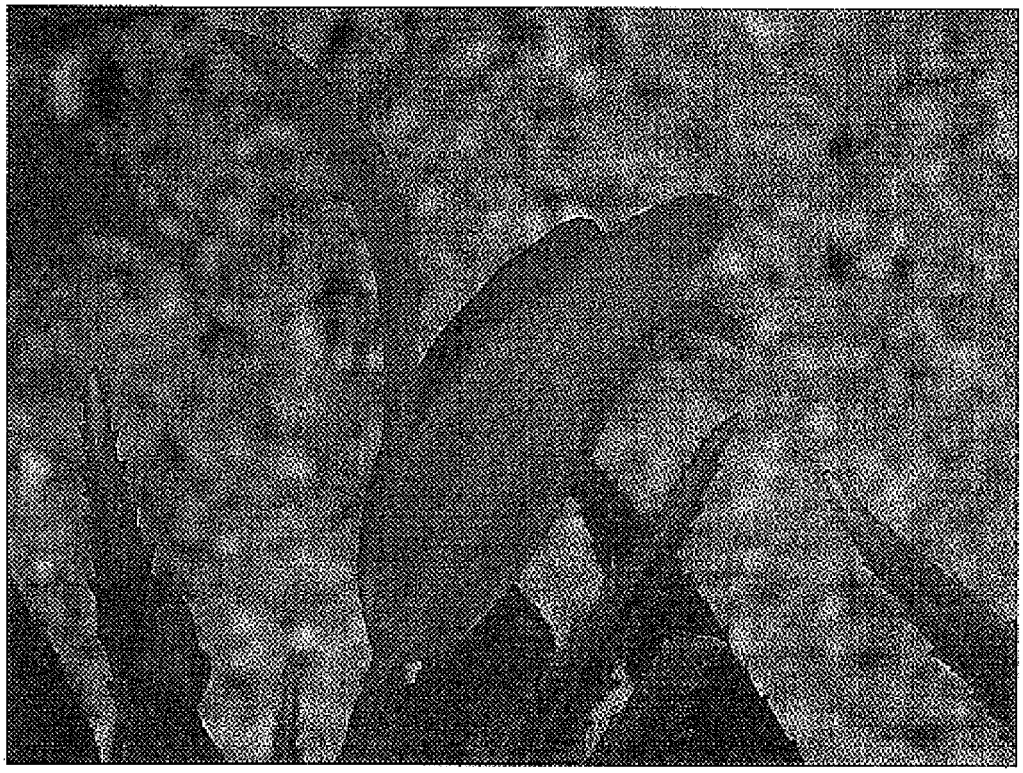

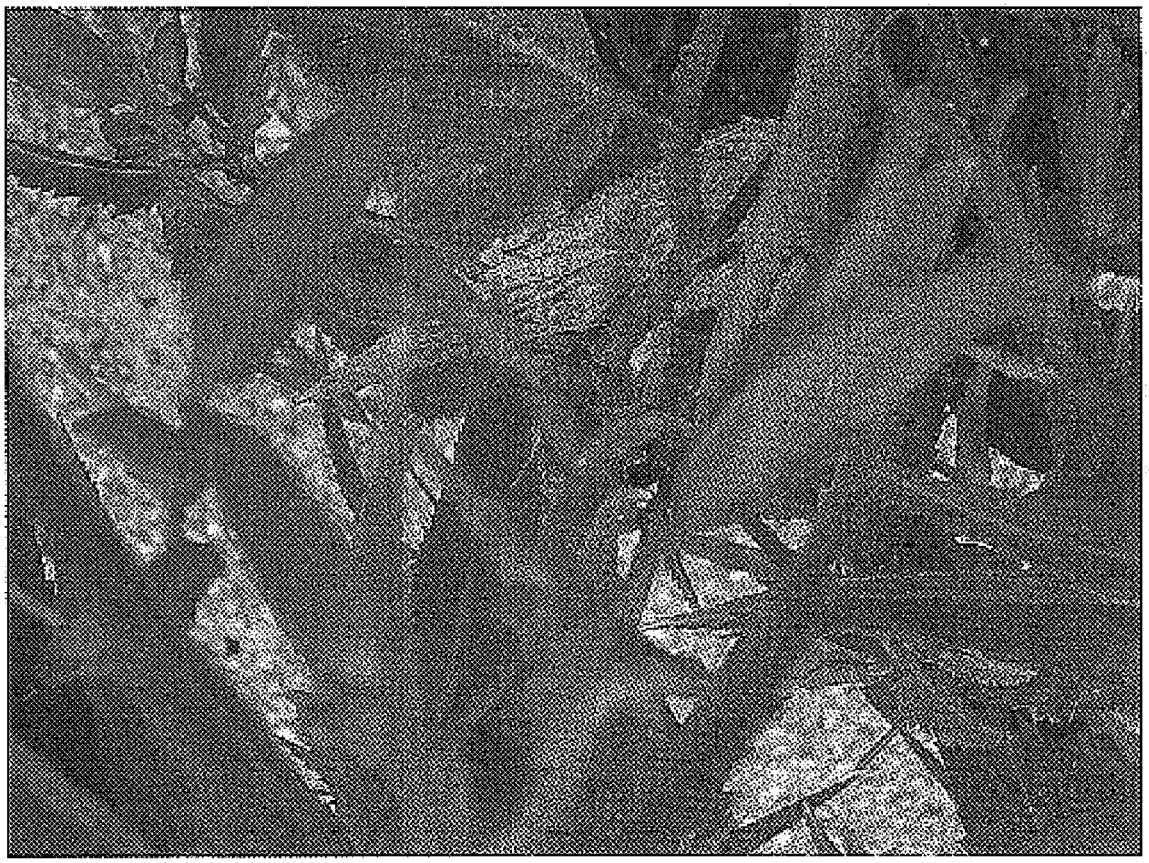

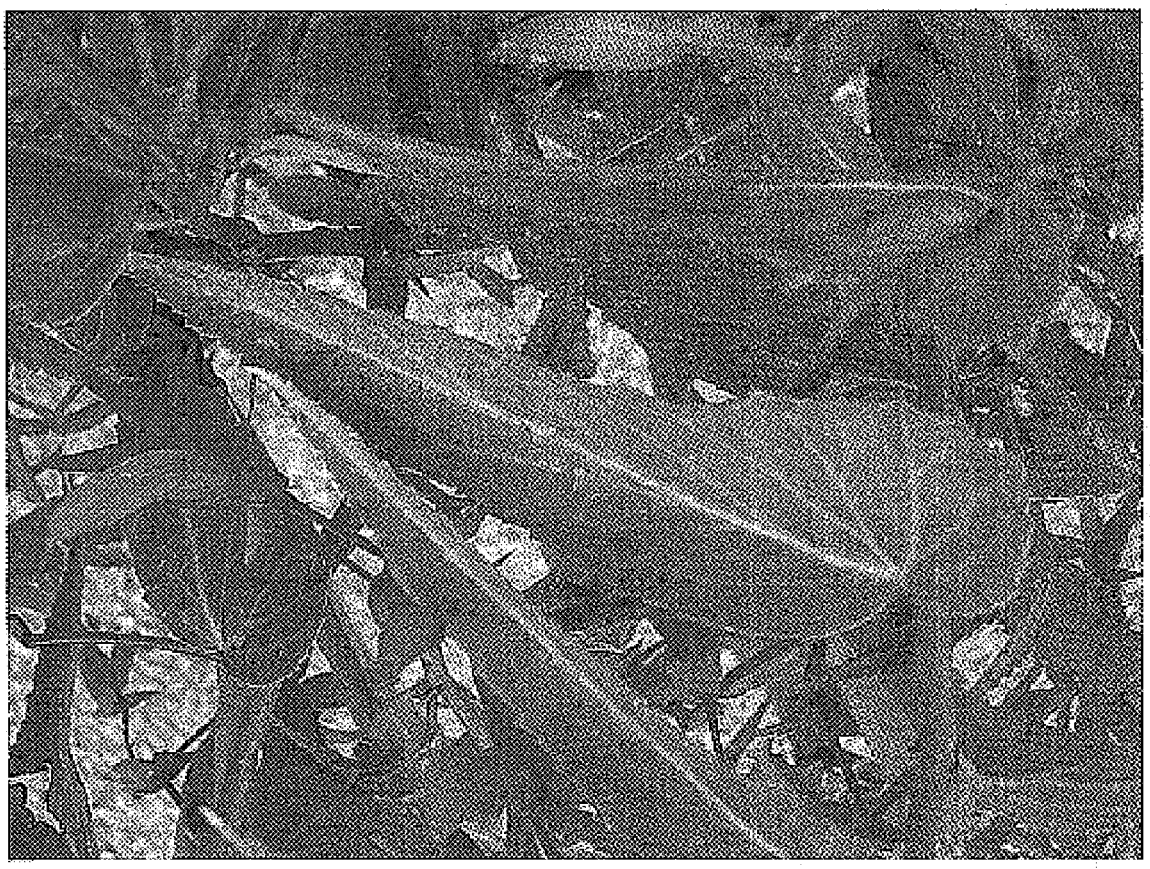

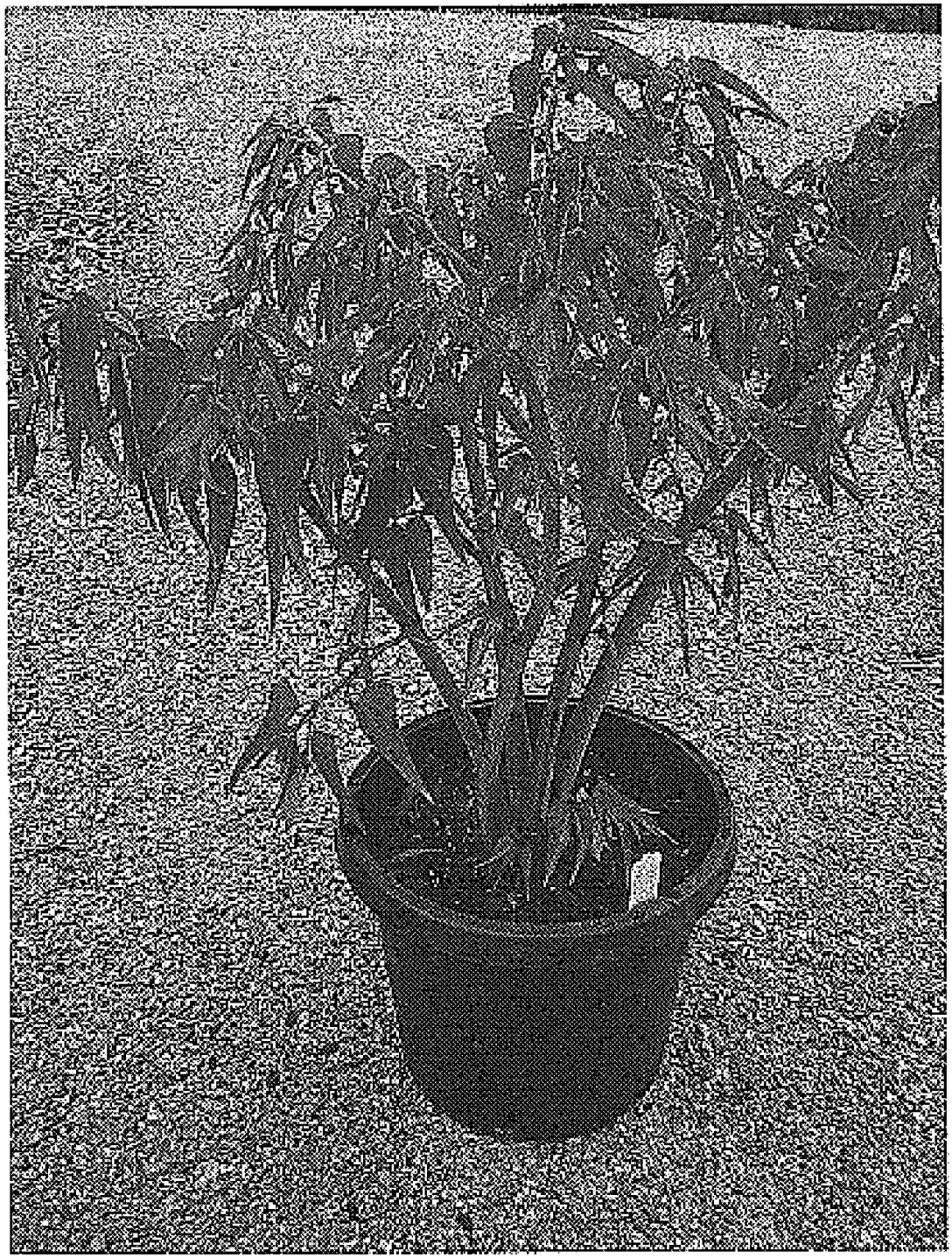

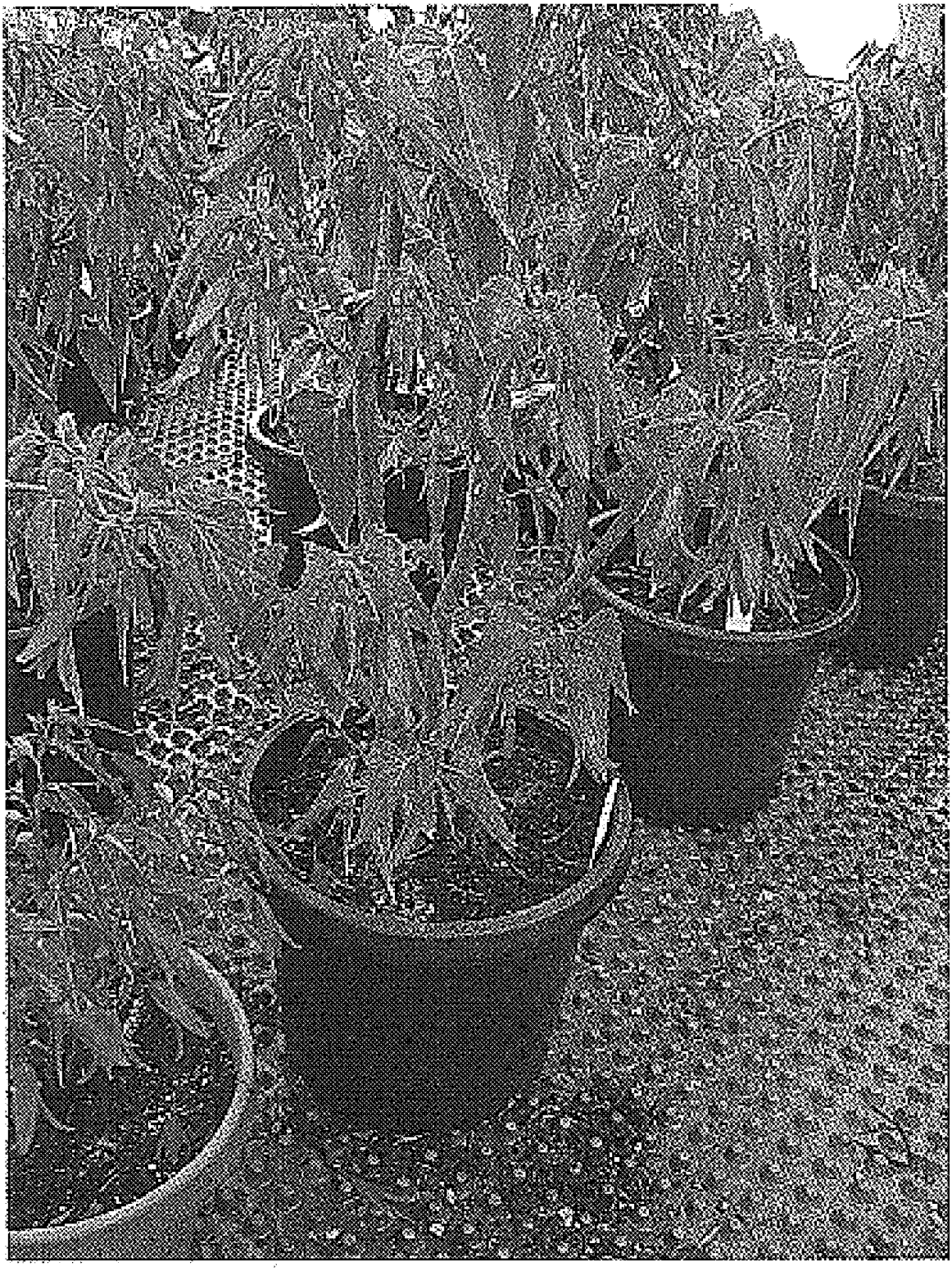

UNITED STATES PATENT AND TRADEMARK OFFICE

CERTIFICATE OF CORRECTION

PATENT NO. : PP 15,108 P2
DATED : August 24, 2004
INVENTOR(S) : Richard James Cross It is certified that error appears in the above-identified patent and that said Letters Patent is hereby corrected as shown below:

Title page,
Item [54], Title, delete, "BONFIRE" and insert -- 'NZCONE' --
Item [50], Varietal Denomination, delete, "Bonfire" and insert -- 'Nzcone' --
Item [57], ABSTRACT, delete, "Bonfire" and insert -- 'Nzcone' --

Column 1,
Lines 3, 9, 26 and 34, delete, "Bonfire" and insert -- 'Nzcone' --

Column 2,
Lines 3, 12, 16, 19, 22, 23-24 and 26, delete, "Bonfire" and insert -- 'Nzcone' --
Line 5, delete "which the gives the foliage a dull" and insert -- which gives the foliage a dull --

Column 4,
Line 30, delete, "Bonfire" and insert -- 'Nzcone' --

Signed and Sealed this

Seventh Day of June, 2005

JON W. DUDAS
*Director of the United States Patent and Trademark Office*